United States Patent [19]

Bryant et al.

[11] Patent Number: 5,441,964
[45] Date of Patent: Aug. 15, 1995

[54] METHODS FOR INHIBITING BONE LOSS USING SUBSTITUTED BENZOTHIOPHENE

[75] Inventors: Henry U. Bryant; Timothy A. Grese, both of Indianapolis, Ind.

[73] Assignee: Eli Lilly and Company, Indianapolis, Ind.

[21] Appl. No.: 137,878

[22] Filed: Oct. 15, 1993

[51] Int. Cl.$^6$ .................. A61K 31/445; A61K 31/40; A61K 31/38

[52] U.S. Cl. .................. 514/324; 514/422; 514/438; 514/443

[58] Field of Search ............. 514/438, 324, 422, 443

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |

FOREIGN PATENT DOCUMENTS

WO93/10113 5/1993 Japan.
WO93/1074 6/1993 WIPO.

OTHER PUBLICATIONS

Jordan et al; *Breast Cancer Research and Treatment*, vol. 10: pp. 31–35; 1987.

Draper et al., "Effects of Raloxifene (LY139481 HC1) on Biochemical Markers of Bone and Lipid Metabolism in Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Overiectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolik et al., "In Vivo and In Vitro Metabolism of Raloxifene", Am. Soc. Bone & Min. Res., Tampa, Sep. 18–22, 1993.

Glasebrook et al., "Multiple Binding Sites for the Anti-estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti-Estrogen, Simulates the Effects of Estrogen in Inhibiting Bone Resorption Through Regulating TGFB-3 Expression in Bone;'-'.Am Soc. for Bone and Min. Res., Tampa, Sep. 18–22, 1993.

*Primary Examiner*—Theodore J. Criares
*Attorney, Agent, or Firm*—James J. Sales; Gerald V. Dahling

[57] ABSTRACT

A method of inhibiting bone loss comprising administering to a human in need of treatment an effective amount of a substituted benzothiophene.

12 Claims, No Drawings

METHODS FOR INHIBITING BONE LOSS USING SUBSTITUTED BENZOTHIOPHENE

BACKGROUND OF THE INVENTION

The mechanism of bone loss is not completely understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects, including post-memopausal women, patients who have undergone hysterectomy, patients who are undergoing or have undergone long-term administration of corticosteroids, patients suffering from Cushing's syndrome, and patients having gonadal dysgenesis. The need for bone repair or replacement also arises locally in the case of bone fracture, non-union, defect, prosthesis implantation, and the like. Further, such need also arises in cases of systemic bone diseases, as in osteoporosis, osteroarthritis, Paget's disease, osteomalacia, osteohalisteresis, multiple myeloma and other forms of cancer and the like.

The current invention provides methods for inhibiting the loss of bone.

SUMMARY OF THE INVENTION

This invention provides methods for the inhibition of bone loss, comprising administering to a human in need of treatment an effective amount of a compound of formula I

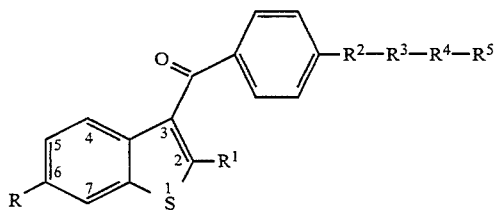

wherein R is hydrogen; hydroxy; $C_1$–$C_6$ alkoxy; a group of the formula —O—C(O)—$R^a$, wherein $R^a$ is hydrogen, $C^1$–$C_6$ alkyl optionally substituted with amino, halo, carbonyl, $C_1$–$C_6$ alkoxycarbonyl, $C_1$–$C_7$ alkanoyloxy, carbamoyl and/or aryl; or $R^a$ is $C_1$–$C_6$ alkenyl optionally substituted with aryl; or $R^a$ is a $C_3$–$C_7$ cycloalkyl; or $R^a$ is aryl optionally substituted with hydroxy, $C_1$–$C_6$ alkyl, $C_1$–$C_6$ alkoxy, and/or halo; or $R^a$ is —O—aryl, said aryl optionally substituted with hydroxy $C_1$–$C_6$ alkyl, $C_1$–$C_6$ alkoxy, and/or halo, or R is a group of the formula —0—$SO_2$—$R^b$ wherein $R^b$ may be $C_1$–$C_6$ alkyl or aryl optionally substituted with $C_1$–$C_6$ alkyl;

or R is carbamoyloxy wherein the nitrogen may be substituted once or twice with $C_1$–$C_6$ alkyl;

or R is a group of the formula —O—C(O)$R^c$—O—($C_1$–$C_6$ alkyl) wherein $R^c$ is a bond or $C_1$–$C_6$ alkanediyl;

$R^1$ is halo, $C_1$–$C_6$ alkyl, $C_1$–$C_7$ alkyl substituted with $C_1$–$C_6$ alkyl, substituted or unsubstituted $C_3$–$C_7$ cycloalkyl, or substituted or unsubstituted $C_3$–$C_7$ cycloalkenyl;

$R^2$ is O or $CH_2$;

$R^3$ is $CH_2$ or $(CH_2)_2$;

$R^4$ is

$CH_2$, or a bond; and $R^5$ is amino, nitrilo optionally substituted once or twice with $C_1$–$C_6$ alkyl; or an N-heterocyclic ring which optionally has another hetero atom selected from N, O, or S in said ring; or a pharmaceutically acceptable salt or solvate thereof.

DETAILED DESCRIPTION OF THE INVENTION

The general chemical terms used in the description of a compound of formula I have their usual meanings. For example, the term "alkyl" by itself or as part of another substitutent means a straight or branched chain alkyl radical having the stated number of carbon atoms such as methyl, ethyl, propyl, and isopropyl and higher homologues and isomers where indicated.

The term "alkoxy" means an alkyl group having the stated number of carbon atoms linked by an oxygen atom, such as methoxy, ethoxy, propoxy, butoxy, pentyloxy, and hexyloxy and also includes branched chain structures such as, for example, isopropoxy and isobutoxy.

The term "$C_1$–$C_7$alkanoyloxy" means a group —O—C(O)—$R^a$ where $R^a$ is hydrogen, or $C_1$–$C_6$ alkyl and includes formyloxy, acetoxy, propanoyloxy, butanoyloxy, pentanoyloxy, hexanoyloxy, and the like and also includes branched chain isomers such as, for example, 2,2-dimethylpropanoyloxy, and 3,3-dimethylbutanoyloxy.

When R is a group of the formula —O—C(O)—$R^c$—O—($C_1$–$C_6$ alkyl) this includes, for example, methoxycarbonyloxy, ethoxycarbonyloxy, propoxycarbonyloxy, butoxycarbonyloxy, methoxyacetoxy, methoxypropanoyloxy, methoxybutanoyloxy, methoxypentanoyloxy, methoxyhexanoyloxy, ethoxyacetoxy, ethoxypropanoyloxy, ethoxybutanoyloxy, ethoxypentanoyloxy, ethoxyhexanoyloxy, propoxyacetoxy, propoxypropanoyloxy, propoxybutanoyloxy, and the like.

Aryl includes groups such as phenyl, naphthyl, thienyl or furyl group that is, as to each group, unsubstituted or monosubstituted with a hydroxyl, halo, $C_1$–$C_3$ alkyl, or $C_1$–$C_3$ alkoxy.

The term "halo" means chloro, fluoro, bromo or iodo.

When $R^5$ is an N-heterocyclic ring which optionally may have another hetero atom selected from N, O, or S in said ring, this includes pyrrolyidino, piperidino, hexamethyleneimino, piperazinyl, morpholinyl, thiomorphorpholinyl, 3-methylpyrroldinyl, 3-methylpiperidinyl, 4-hydroxy piperidinyl, 4-methylpiperazinyl, 4-ethyl piperazihyl, 2,3-dihydroindolyl, and 1,2,3,4-tetrahydroisoquinolyl. Generally, the heterocyclic group containing the nitrogen atom is a 5–6 membered ring.

Substituted $C_3$–$C_7$ cycloalkyl and substituted $C_3$–$C_7$ cycloalkenyl are those groups substituted with $C_1$–$C_6$ alkyl, hydroxyl, —O—C(O)$R^a$, wherein $R^a$ is as defined before, and/or an oxo group. Examples of such are 3-methylcycopentyl, 3-hydroxy cyclopentyl, 2-methylcyclohexyl, 3-methylcycohexyl, 4-methylcyclohexyl, 4-acetoxy cyclohexyl, 4-benzoyloxy cyclohexyl, 4-oxo cyclohexyl and 2-methyl cycloheptyl.

Specific examples of the compounds of the above-mentioned Formula I offered by the present invention include the following:

(6-hydroxy-2-cyclopentylbenzo[b]thien-3-yl)[4-[2-[1-4-methylpiperazinyl)] ethoxy]phenyl]methanone,
(6-hydroxy-2-cyclohexylbenzo[b]thien-3-yl)[4-[2-[1-(3-methylpyrrolidinyl)] ethoxy]phenyl]methanone,
(6-hydroxy-2-cyclohexylbenzo[b]thien-3-yl)[4-[2-(N-thiomorpholinyl)ethoxy]phenyl]methanone,
(6-methanesulfonyloxy-2-cyclohexylbenzo[b]thien-3-yl)[4-[2-(1-piperidinyl)ethoxy]phenyl]methanone,
(6-hydroxy-2-cycloheptylbenzo[b]thien-3-yl)[4-2-(N-morpholinyl)ethoxy]phenyl]methanone,
(6-hydroxy-2-cyclooctylbenzo[b]thien-3-yl)[4-[2-(1-piperidinyl)ethoxy]phenyl]methanone,
(6-hydroxy-2-cyclododecylbenzo[b]thien-3-yl)[4-[2-(1-pyrrolidinyl)ethoxy]phenyl]methanone,
[6-hydroxy-2-(2-methylcyclohexylbenzo[b]thien-3-yl][4-[2-(dimethylamino)ethoxy]phenyl]methanone,
[6-hydroxy-2-(4-hydroxycyclohexyl)benzo[b]thien-3-yl][4-[2-(1-pyrrolidinyl) ethoxy]phenyl]methanone,
[6-hydroxy-2-(4-hydroxycyclohexyl)benzo[b]thien-3-yl][4-[2-(1-homopiperidinyl) ethoxy]phenyl]methanone,
(6-hydroxy-2-isopropylbenzo[b]thien-3-yl)[4-[2-(diethylamino)ethoxy]phenyl]methanone,
(6-hydroxy-2-isopropylbenzo[b]thien-3-yl)[4-[2-(1-homopiperidinyl)ethoxy]phenyl]methanone,
(6-hydroxy-2-sec-butylbenzo[b]thien-3-yl)[4-[2-(1-piperidinyl)ethoxy]phenyl]methanone,
(6-hydroxy-2-cyclohexylbenzo[b]thien-3-yl)[4-[3-(dimethylamino)propoxy]phenyl]methanone,
[6-hydroxy-2-(3-methylcyclohexyl)benzo[b]thien-3-yl][4-[3-(1-piperidinyl) propoxy]phenyl]methanone,
(6-hydroxy-2-isopropylbenzo[b]thien-3-yl)[4-[3-(1-piperidinyl)propoxy]phenyl]methanone,
(6-hydroxy-2-cyclohexylbenzo[b]thien-3-yl)[4-[2(Diethylcarbamoyl)ethyl]phenyl]methanone,
[6-hydroxy-2-(3methylcyclohexyl)benzo[b]thien-3-yl][4-[2-(1-piperidinylcarbonyl)ethyl]methanone,
(6-hydroxy-2-isopropylbenzo[b]thien-3-yl)[4-[2-(1-piperidinylcarbonyl)ethyl]phenyl]methanone.
(6-hydroxy-2-cyclohexylbenzo[b]thien-3-yl)[4-[3-(1-homopiperidinyl)propyl]phenyl]methanone,
(6-hydroxy-2-cyclohexylbenzo[b]thien-3-yl)[4-[3-(N-morpholinyl)propyl]phenyl]methanone,
(6-hydroxy-2-isopropylbenzo[b]thien-3-yl)[4-[3-(1-pyrrolidinyl)propyl]phenyl]methanone,
(6-hydroxy-2-cyclopentylbenzo[b]thien-3-yl)[4-[3-(1-pyrrolidinylcarbonyl)propyl]phenyl]methanone,
[6-hydroxy-2-(2-methylcyclohexyl)benzo[b]thien-3-yl][4-[3-(1-piperidinylcarbonyl) propyl]phenyl]methanone,
(6-hydroxy-2-cyclopentylbenzo[b]thien-3-yl)[4-[4-(1-piperidinyl)butyl]methanone, and
(6-hydroxy-2-isopropylbenzo[b]thien-3-yl)[4-[4-(1-pyrrolidinyl)butyl]phenyl]methanone.

The current invention concerns the discovery that the compounds of formula I are useful for inhibiting bone loss. The methods of treatment provided by this invention are practiced by administering to a human in need of inhibition of bone loss a dose of a compound of formula I or a pharmaceutically acceptable salt or solvate thereof, that is effective to inhibit bone loss. The present method includes both medical therapeutic and/or prophylactic treatment, as appropriate. Generally, the compound is formulated with common excipients, diluents or carriers, and compressed into tablets, or formulated as elixirs or solutions for convenient oral administration, or administered by the intramuscular or intravenous routes. The compounds can be administered transdermally.

The method also includes the administration of a compound of formula I and estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin (a commercial preparation of conjugated estrogens isolated from natural sources—Ayerst), and the like.

All of the compounds used in the methods of the current invention can be made according to established or analogous procedures, such as those detailed in U.S. Pat. Nos. 4,133,814, 4,418,068, and 4,380,635 all of which are incorporated by reference herein. Modifications to the above methods may be necessary to accommodate reactive functionalities of particular substituents. Such modifications would be both apparent to, and readily ascertained by, those skilled in the art.

With the present invention, the compound of the above-mentioned Formula I, or a salt thereof, can be manufactured, for example, by (a) allowing a compound expressed by the formula

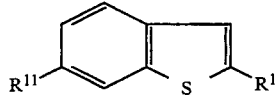

(II)

(where $R^{11}$ is a hydrogen atom or a lower alkyl group, and $R^1$ is defined the same as above)to react with a compound expressed by the formula

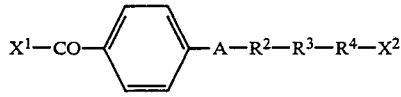

(III)

(Where $X^1$ and $X^2$ are each a halogen atom, and $R^2$, $R^3$ and $R^4$ are defined the same as above), and then allowing the compound thus obtained, which is expressed by the formula

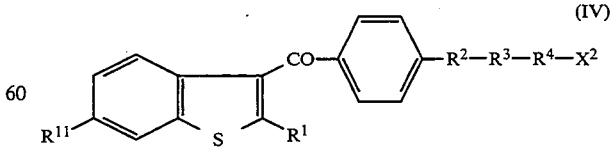

(IV)

(where $R^{11}$, $R^1$, $R^2$, $R^3$, $R^4$ and $X^2$ are defined the same as above), to react with a group represented by $R^5$ or (b) allowing the compound of the above-mentioned Formula II to react with a compound expressed by the formula

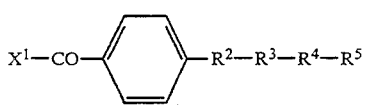

and then (c) converting the ring $R^{11}$ in the compound thus obtained, which is expressed by the formula

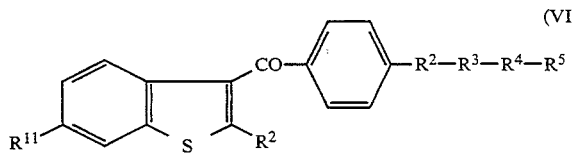

as needed into a carbamoyloxy group that is unsubstituted or has been substituted with a hydroxy group, an acyloxy group, or an N,N-di-lower alkyl group, and then converting the compound thus obtained into a salt as needed.

The first step in the above method (a) is to allow the compound of the above Formula II to react with the compound from the above Formula III.

This reaction can be conducted according to a Friedel-Crafts acylation reaction, which is itself already known. In specific terms it can be conducted in an inert organic solvent (such as dichloromethane, 1,2-dichloroethane, chloroform, or another such halogenated hydrocarbon; benzene, chlorobenzene, or another such aromatic hydrocarbon; petroleum ether, hexane, or another such alkane; or nitrobenzene, nitromethane, or another such nitrohydrocarbon) and in the presence of a catalyst (such as aluminum chloride, aluminum bromide, zinc chloride, boron trifluoride, titanium tetrachloride, stannic chloride, or another such Lewis acid). The reaction temperature is generally from about room temperature to the reflux temperature of the reaction mixture, and a temperature ranging from room temperature to 100° C. is preferable.

As to the amount in which the compound from the above Formula III is used with respect to the compound from the above Formula II, using the compound from Formula III in a proportion of at least one mole, and preferably 1.1 to five moles, per mole of the compound from Formula II is advantageous.

As to the amount in which the catalyst is used, the catalyst usually should be used in a proportion of at least one mole, and preferably about 1.5 to 10 moles, per mole of the compound from the above Formula II.

This reaction produces the compound from the above Formula IV, and this compound is then allowed to react with the amine ($R^5$).

The reaction between the compound from the above Formula IV and the amine ($R^5$) generally can be conducted in the absence of a solvent or in an inert solvent (such as ethyl ether, tetrahydrofuran, dioxane, or another such ether; dimethylformamide, dimethylacetamide, or another such amide; benzene, toluene, or another such aromatic hydrocarbon; or dimethyl sulfoxide) The reaction temperature is usually between room temperature and the reflux temperature of the reaction mixture, and a range of 35° C. to the reflux temperature of the reaction mixture is preferable.

As to the amount in which the amine ($R^5$) is used with respect to the compound from the above Formula IV, using the amine ($R^5$) in an amount of one mole, and usually about 1.5 to 10 moles, per mole of the compound from Formula IV is favorable. When the reaction is conducted in the absence of a solvent, the amine ($R^5$) can be used in an excess amount and made to serve as a solvent as well.

It is preferable for the above reaction to be conducted in the presence of a deoxidant, such as pyridine, triethylamine, or another such organic base, or calcium carbonate, sodium carbonate, or another such inorganic base, but the amine is usually used in an excess amount and also made to serve as a deoxidant.

With the above method (b), the compound from the above Formula II is allowed to react with the compound from the above Formula VI.

The reaction can be conducted in the same manner as described for the reaction between the compound from the above Formula II and the compound from the above Formula III in the above method (a).

This produces a compound in which R in the compound from the above Formula I, which is the objective of the present invention, is a hydrogen atom or a lower alkyl group, i.e., the compound from the above Formula VI, and this compound can be converted as needed into the compound from the above Formula I in which R is a carbamoyloxy group that is unsubstituted or has been substituted with a hydroxy group, an acyloxy group, or an N,N-di-lower alkyl group.

The conversion to the compound from the above Formula I in which R is a hydroxy group can be accomplished by subjecting the compound from the above Formula VI in which $R^{11}$ is a lower alkyl group to a dealkylation reaction.

This dealkylation reaction generally can be conducted by treatment in an inert solvent (such as dichloromethane, chloroform, or another such halogen hydrocarbon; or benzene, toluene, or another such aromatic hydrocarbon), in the presence of both ethane thiol, dimethyl sulfide, or another such sulfur compound and aluminum chloride, boron trifluoride, or another such Lewis acid, and under heating preferably at the reflux temperature of the reaction mixture.

The conversion to the compound from the above Formula I in which R is an acyloxy group can be accomplished easily by acylating the compound from the above Formula I in which R is a hydroxy group by allowing it to react with an acyl halide in pyridine, for example, according to a known method.

The conversion to the compound from the above Formula I in which R is a carbamoyloxy group that is unsubstituted or has been substituted with an N,N-di-lower alkyl group can also be accomplished easily by allowing the compound from the above Formula I in which R is a hydroxy group to react with a substituted or unsubstituted carbamoyl chloride in pyridine, for example.

Of the compounds from the above Formula I of the present invention, a compound in which $R^4$ is —$CH_2$— can also be manufactured by another method, in which the compound expressed by the following formula

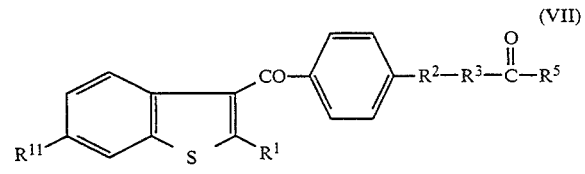

The reduction of the compound from Formula VII can be accomplished, for example, by treatment with lithium aluminum hydride in tetrahydrofuran, dioxane, or another such solvent under heating and reflux. The oxidation of the compound thus obtained, which is expressed by the following formula

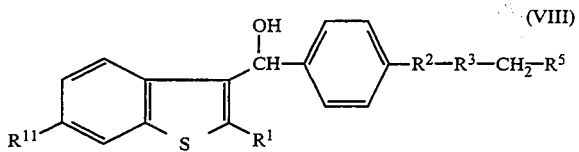
(VIII)

can be easily accomplished, for example, by treating this compound with chromium trioxide in pyridine.

When $R^1$ in the compound from the above Formula I of the present invention is a cycloalkyl group or cycloalkenyl group that has been substituted with a hydroxy group, it may be manufactured by subjecting the compound from Formula I in which $R^1$ is a cycloalkyl group or cycloalkenyl group that has been substituted with an oxo group to reduction with sodium borohydride or another such complex metal hydride in tetahydrofuran or another such solvent, for example.

The compound from Formula I in which $R^1$ is a cycloalkyl group or cycloalkenyl group that has been substituted with an acyloxy group can be manufactured by acylating according to a known method the compound from Formula I in which $R^1$ is a cycloalkenyl group that has been substituted with a hydroxy group. In this reaction, when the compound from Formula I is one in which R is a hydroxy group R will also be acylated at the same time and converted into an acyloxy group.

The compound from the above Formula II, which is a starting material of the compound of the present invention, can be synthesized according to the following Reaction Formula 1.

Reaction Formula 1

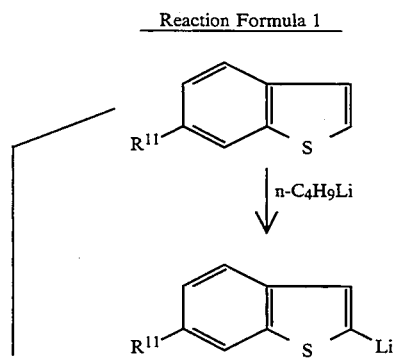

-continued
Reaction Formula 1

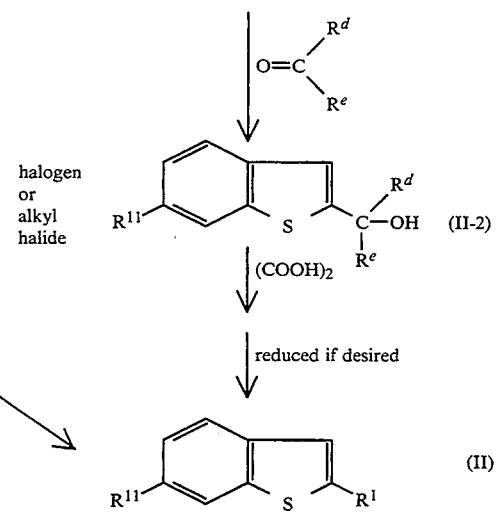

In the above formulas, $R^d$ and $R^e$ are each a lower alkyl group, or join together with the carbon atom to which they are bonded and form a cycloalkyl group that may be substituted with an oxo group or a lower alkyl group. $R^{11}$ is defined the same as above.

The compound from Formula II in which $R^d$ is a cycloalkyl group or cycloalkenyl group that has been substituted with a hydroxy group or an acyloxy group can be synthesized by converting a compound in which $R^1$ is a cycloalkyl group or cycloalkenyl group that has been substituted with an oxo group in the same manner as described for the conversion of $R^1$ in the compound from Formula I.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. In addition, some of the formula I compounds may form solvates with water or organic solvents such as ethanol. These solvates are also contemplated for use in the methods of this invention.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds either alone or in combination with estrogen can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds either alone or in combination with estrogen can also be formulated as elixirs or solutions for convenient oral administration or as solutions appropriate for parenteral administration, for instance by intramuscular, subcutaneous or intravenous routes. Additionally, the compounds either alone or in combination with estrogen are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit bone loss, according to this invention will depend upon the severity of the condition, the route of administration, and related factors that will be decided by the attending physician. Generally, accepted and effective daily doses will be from about 0.1 to about 1000 mg, and more typically from about 200 to about 600 mg. Such dosages will be administered to a subject in need of treatment from once to about three times each day, or more often as needed to effectively inhibit bone loss. Generally, accepted and effective daily doses of estrogen will be from about 0.01 to about 4.0 mg, and more typically from about 0.1 to about 2.0 mg. Such doses are administered to a subject in need of treatment from once to about three times a day, or more often as needed.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female). For such purposes the following oral dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules. The components are blended and compressed to form tablets.

Alternatively, tablets each containing 0.1–1000 mg of active ingredient are made up as follows:

Formulation 2: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 3: Suspensions

| Ingredient | Quantity (mg/5 ml) |
|---|---|
| Active ingredient | 0.1–1000 mg |
| Sodium carboxymethyl cellulose | 50 mg |

-continued

| Ingredient | Quantity (mg/5 ml) |
| --- | --- |
| Syrup | 1.25 mg |
| Benzoic acid solution | 0.10 mL |
| Flavor | q.v. |
| Color | q.v. |
| Purified water to | 5 mL | medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following nonlimiting test examples illustrate the methods of this invention.

Test Procedure

Six month old, female Sprague Dawley rats (weight range of 275 to 350 g; Harlan Sprague Dawley, Indianapolis, Ind.) are used in these studies. Ovariectomies (or a sham surgical procedure for controls) are performed by the vendor. The animals are shipped the day following surgery and housed in hanging wire cages. Room temperature is maintained at $22.2° \pm 1.7°$ C. with a minimum relative humidity of 40%. The photoperiod in the room is 12 hr light and 12 hr dark, with light onset at 0600 hr. The animals have ad lib access to food (Teklad diet, TD 89222, 0.5% calcium, 0.4% phosphorus; Madison, Wis.) and water. The animals are allowed one day to acclimate to these conditions prior to experimental manipulation.

The test compound is prepared as described and a suspension is prepared in 20% $\beta$-cyclodextrin (CDX). 20% CDX is used as the control vehicle. 17$\alpha$-Ethynylestradiol (obtained from Sigma Chemical Co.; St. Louis, Mo.) is dissolved in 20% CDX and is employed as an internal standard for these studies.

On the third day post-ovariectomy dosing with test compounds is initiated. Oral gavages 20% CDX, 135495 (0.1 to 10 mg.kg) or 17$\alpha$-ethynyl-estradiol(100 $\mu$g/kg) are delivered daily for 35 consecutive days. On the evening following the final dose, the animals are fasted. The animals are anesthetized with a mixture of Keta-set ® and Rompun ® (67 and 6.7 mg/kg, respectively) the next morning and a 3 ml sample of blood is obtained by cardiac puncture. The animals are then asphyxiated with carbon dioxide and body weight and uterine weight are recorded. The left femur is removed from each animal, cleaned and frozen for subsequent x-ray evaluation.

The distal end of the femur is x-rayed using a Norland NXR-1200 x-ray machine with a voltage of 47 kV and contrast at 4.5. Digitilized x-ray images are transferred directly to a Macintosh comuter station and image analysis of the x-ray scan is conducted using the Ultimage ® software program. Quantitation is achieved by measuring the total number of pixels in a standard region of interest proximal to the growth plate, over a gray scale range of zero to 60.

Experimental groups consist of 6 to 8 rats. Data for control and treated rats are compared by one way analysis of variance (ANOVA).

In summary, the compounds exhibit a positive impact on inhibition of bone loss under this assay.

EXAMPLE 1

1 mL of pyrrolidine is added to 30 mg of (6-methoxy-2-cyclopentylbenzo [b]thien-3-yl)[4-(2-chloroethoxy)-phenyl]methanone, and this mixture is heated and refluxed for one hour. The mixture is condensed under reduced pressure to distill off the pyrrolidine, and then is refined by TLC (developing solvent was chloroform:methanol=19:1) which gives 28 mg of (6-methoxy-2-cyclopentylbenzo [b]thien-3-yl)[4-[2-(1-pyrrolidinyl)ethoxy)phenyl]methanone.

1H-NMR (CDCL3,$\delta$): 0.94–2.47 (12H,m), 2.55–2.79 (4H,m), 2.94 (2H,t, J=6Hz), 3.41 (1H, m), 3.84 (3H, s), 4.19 (2H, t, J=6 Hz), 6.69–7.87 (7H,m). MS (m/z): 449 (M+) , 84.

The following listed compounds may be synthesized in the same manner as in Example 1.

(6-methoxy-2-cyclopentylbenzo[b]thien-3-yl)[4-[2-(1-homopiperidinyl)]ethoxy]phenyl]methanone (6-methoxy-2-cyclopentylbenzo[b]thien-3-yl)[4-[2-[1-3-methylpiperidinyl)]ethoxy 'phenyl]methanone (6-methoxy-2-cyclohexylbenzo[b]thien-3-yl)[4-[2-[1-(4-methylpiperidinyl)]ethoxy]phenyl]methanone (6-methoxy-2-cyclohexylbenzo[b]thien-3-yl)[4-[2-[2-(1,2,3,4-tetrahydroisoquinolinyl)]ethoxy]phenyl]methanone (6-methoxy-2-cyclohexylbenzo[b]thien-3-yl[4-[2-[1-(4-hydroxypiperidinyl)]ethoxy]phenyl]methanone (6-methoxy-2-cyclohexylbenzo[b]thien-3-yl)[4-[2-(diethylamino) ethoxy]phenyl]methanone (6-methoxy-2-cycloheptylbenzo[b]thien-3-yl)[4-[2-(1-pyrrolidinyl) ethoxy]phenyl]methanone (6-methoxy-2-cycloheptylbenzo[b]thien-3-yl)[4-[2-(1-homopiperidinyl) ethoxy]phenyl]methanone (6-methoxy-2-cycloheptylbenzo[b]thien-3-yl)[4-[2-[1-(3-methylpiperidinyl)]ethoxy]phenyl]methanone (6-methoxy-2-(2-methylcyclohexyl)benzo[b]thien-3-yl][4-[2-(1-pyrrolidinyl) ethoxy]phenyl]methanone

[6-methoxy-2-(2-methylcyclohexyl)benzo[b]thien-3-yl][4-[2-(1-piperidinyl) ethoxy]phenyl]methanone

[6-methoxy-2-(2-methylcyclohexyl)benzo[b]thien-3-yl][4-[2-(1-homopiperidinyl) ethoxy]phenyl]methanone

[6-methoxy-2-(3-methylcyclohexyl)benzo[b]thien-3-yl][4-[2-(1-pyrrolidinyl) ethoxy]phenyl]methanone

[6-methoxy-2-(3-methylcyclohexyl)benzo[b]thien-3-yl][4-[2-(1-piperidinyl) ethoxy]phenyl]methanone

[6-methoxy-2-(3-methylcyclohexyl)benzo[b]thien-3-yl][4-[2-(1-homopiperidinyl) ethoxy]phenyl]methanone

[6-methoxy-2-(3-methylcyclohexyl)benzo[b]thien-3-yl][4-[2-[1-(3-methylpiperidinyl)ethoxy]phenyl]methanone (6-methoxy-2-cyclopentylbenzo[b]thien-3-yl)[4-[3-(1-piperidinyl) propoxy]phenyl]methanone (6-methoxy-2-cyclohexylbenzo[b]thien-3-yl)[4-[3-(diethylamino)propoxy]phenyl]methanone (6-methoxy-2-cyclohexylbenzo[b]thien-3-yl)[4-[3-(1-pyrrolidinyl)propoxy]phenyl]methanone (6-methoxy-2-cyclohexylbenzo[b]thien-3-yl)[4-[3-(1-piperidinyl)propoxy]phenyl]methanone (6-methoxy-2-cyclohexylbenzo[b]thien-3-yl)[4-[3-(1homopiperidinyl) propoxy]phenyl]methanone (6-methoxy-2-cyclohexylbenzo[b]thien-3-yl)[4-[3-[1-(3-methylpiperidinyl)]propoxy]phenyl]methanone (6-methoxy-2-cyclohexylbenzo[b]thien-3-yl)[4-[3-[1-(4-methylpiperazinyl)]propoxy]phenyl]methanone (6-methoxy-2-cyclohexylbenzo[b]thien-3-yl)[4-[3-[2-(1,2,3,4-tetrahydroisoquinolinyl)]propoxy]phenyl]-methanone
(6-methoxy-2-cycloheptylbenzo[b]thien-3-yl)[4-[3-(1-pyrrolidinyl) propoxy]phenyl]methanone
(6-methoxy-2-cycloheptylbenzo[b]thien-3-yl)[4-[3-(1-piperidinyl) propoxy]phenyl]methanone
(6-methoxy-2-cycloheptylbenzo[b]thien-3-yl)[4-[3-(1-homopiperidinyl) propoxy]phenyl]methanone
(6-methoxy-2-cyclododecylbenzo[b]thien-3-yl)[4-[2-(1-piperidinyl) ethoxy]phenyl]methanone
(6-methoxy-2-isopropylbenzo[b]thien-3-yl)[4-[2-(1-piperidinyl) ethoxy]phenyl]methanone
(6-methoxy-2-isopropylbenzo[b]thien-3-yl)[4-[2-(1-piperidinyl) ethoxy]phenyl]methanone

EXAMPLE 2

49 mg of sodium hydride is added to a THF solution of 0.2 mL of pyrrolidine, and this mixture is agitated for one hour at room temperature. To this is added 54 mg of (6-methoxy-2-cyclohexylbenzo[b]thien-3-yl)[4-(2-chloroethoxy)phenyl]methanone, and this mixture is heated and refluxed for ten hours. Water is added and extracted with ethyl acetate, and this extract is refined by TLC (developing solvent was chloroform:methanol=19:1), which gives 12 mg of (6-methoxy-2-cyclohexylbenzo[b]thien-3-yl) [4-[2-(1-pyrrolidinyl)ethoxy)phenyl]methanone.

$^1$H-NMR(CDCL$_3$,$\delta$): 1.15–2.10 (14H, m), 2.67–2.86 (4H, m), 3.00 (2H, t, J=5.7 Hz), 3.4 (1H, m), 3.84 (3H,s), 4.23(2H, t, J=5.7 Hz), 6.78–7.86 (7H, m). MS(m/z): 463 (M+), 84.

The following compounds may be synthesized in the same manner as in Example 2.
(6-methoxy-2-cyclohexylbenzo[b]thien-3-yl)[4-[2-(1-homopiperidinyl)ethoxy]phenyl]methanone
(6-methoxy-2-cyclohexylbenzo[b]thien-3-yl)[4-[2-(N-morpholinyl)ethoxy]phenyl]methanone

EXAMPLE 3

50 mg of (6-methoxy-2-cyclohexylbenzo[b]thien-3-yl)[4-(2-chloroethoxy)phenyl]methanone is dissolved in 5 mL of DMF, 20 mg of potassium iodide and 0.5 mL of 3-methylpiperidine are added, and this mixture is agitated for eight hours at approximately 40° C., for two days at room temperature, and for two hours at approximately 50° C. The reaction mixture is condensed underreduced pressure, a saturated aqueous solution of sodium hydrogencarbonate is added, and an extraction is performed with ethyl acetate. The organic layer is washed with saturated salt water, after which it is dried with anhydrous magnesium sulfate. The solvent is distilled off, and the residue is refined by TLC (developing solvent: chloroform), which gives 31 mg of (6-methoxy-2-cyclohexylbenzo[b]thien-3-yl)[4-[2-[1-(3-methyl-piperidinyl)]ethoxy]phenyl]methanone.

1H-NMR(CKCL3,): 0.87 (3H, d, J=5.7 Hz), 1.01–2.76 (17H, m), 2.73–3.11(5H, m), 3.84 (3H, s), 4.18(2H, t, J=6 Hz), 6.75–7.88 (7H, m). MS (m/z): 491 (M+), 112.

The following compounds may be synthesized in the same manner as in Example 3.
(6-methoxy-2-cyclohexylbenzo[b]thien-3-yl)]4-[3-(N-morpholinyl)propoxy]phenyl]methanone

EXAMPLE 4

88 mg of chromium trioxide is added to 5 mL of pyridine to produce a yellow solution with the consistency of gruel, to which is added a pyridine solution of 105 mg of (6-methoxy-2-cyclohexylbenzo[b]thien-3-yl)[4-[3-(1-poperidinyl propyl]phenyl]methanol, and this mixture is agitated for one hour at room temperature. Ice is put into the reaction mixture, after the organic layer is extracted with ethyl acetate and then dried with anhydrous magnesium sulfate. The solvent is distilled off, and the crude product thus obtained is refined by TLC (developing solvent was chloroform:methanol=19:1), which gives 47 mg of (6-methoxy-2-cyclopentylbenzo[b]thien-3-yl)[4-[3-(1-piperidinyl)-propyl]phenyl]methanone.

$^1$H-NMR(CDCl$_3$,$\delta$): 1.15–2.09 (16H,m), 2.30–2.57 (6H,m), 2.62–2.96 (4H, m), 3.84(3H, s), 6.78–7.79(7H,m). MS (m/z): 475 (M+), 98.

The following compounds may be synthesized in the same manner as in Example 4.
(6-methoxy-2-cycloheptylbenzo[b]thien-3-yl)[4-[3-(1-piperidinyl)propyl]phenyl]methanone
(6-methoxy-2-cyclohexylbenzo[b]thien-3-yl)[4-[3-(dimethylamino)propyl]phenyl]methanone
(6-methoxy-2-cyclohexylbenzo[b]thien-3-yl)[4-[3-(1-pyrrolidinyl)propyl]phenyl]methanone
(6-methoxy-2-cylohexylbenzo[b]thien-3-yl)[4-[4-(1-pyrrolidinyl)butyl]phenyl]methanone

EXAMPLE 5

50 mg of (6-methoxy-2-(4-oxocyclohexyl)benzo[b]thien-3-yl][4-[2-(1-piperidinyl) ethoxy]phenyl]methanone is dissolved in 4 mL of methanol and 0.5 mL of THF and cooled with ice. 6 mg of sodium borohydride is added, and this mixture is agitated at 0° C. for 15 minutes. Water is added to the reaction mixture, and the organic layer is extracted with ethyl acetate, then washed with water and dried with anhydrous sodium sulfate, after which the solvent is distilled off. The crude product thus obtained is refined by TLC (developing solvent was chloroform:methanol=19:1), which gives 32 mg of [6-methoxy-2-(4-hydroxycyclohexyl)-benzo[b]thien-3-yl][4-[2-(1-(piperidinyl)ethoxy]phenyl]-methanone.

$^1$H-NMR(CDCL3): 1.10–2.20(14H,m), 2.60–3.00 (4H,m), 3.06(2H,t, J=6Hz), 3.60 (2H,m), 3.85 (3H, s), 4.41 (2H, t,J=6Hz), 6.70–7.30 (5H,m), 7.80(2H, d,J=9 HZ). MS(m/z): 493(M+), 382, 323, 98.

EXAMPLE 1

200 mg of aluminum chloride is added to 20 mL of dichloromethane, and while this mixture is being agitated at 0° C., 10 mL of a dichloromethane solution of 0.3 mL of oxalyl chloride is added dripwise and agitated for ten minutes at 0° C. 2 mL of a dichloromethane solution of 100 mg of 4-phenylbutylpyrrolidine is added dropwise and agitated for 30 minutes at room temperature. Water is added, and the organic layer is extracted with dichloromethane and dried with anhydrous magnesium sulfate, after which it is condensed. The residue is dissolved in 20 mL of dichloromethane, 100 mg of 6-methoxy-2-cyclohexylbenzo[b]thiophene and 200 mg of aluminum chloride are added, and this mixture is agitated for two hours at room temperature. 1 mL of THF, 0.3 mL of 20% hydrochloric acid, and 1 mL of water are added to the reaction mixture at 25° C. or below, after which a saturated aqueous solution of sodium hydrogencarbonate is added to render the solution alkaline, and the organic layer is extracted with dichloromethane and dried with anhydrous magnesium sulfate. The solvent is distilled off, and the crude product thus obtained is refined by TLC (developing solvent was chloroform: n-hexane=1:5), which gives 54 mg of (6-methoxy-2-cyclohexylbenzo[b]thien-3-yl)[4-[3-(1-pyrrolidinylcarbonyl)propyl]phenyl]methanone.

MS (m/z): 489 (M+), 113.

The following compounds may be synthesized in the same manner as in Example 6.

(6-methoxy-2-cyclohexylbenzo[b]thien-3-yl)[4-[3-(1-piperidinylcarbonyl) propyl]phenyl]methanone
(6-methoxy-2-cyclohexylbenzo[b]thien-3-yl)[4-[4-(1-piperidinyl butyl]phenyl]methanone
(6-methoxy-2-cyclohexylbenzo[b]thien-3-yl)[4-[3-(dimethylcarbamoyl)propyl]phenyl]methanone

EXAMPLE 7

35 mg of (6-methoxy-2-cyclopentylbenzo[b]thien-3-yl)[4-[2-(dimethylamino)ethoxy]phenyl]methanone is dissolved in 5 mL of dichloromethane, 65 mg of aluminum chloride and 0.03 mL of ethanethiol are added, and this mixture is agitated for two hours at room temperature. 0.3 mL of THF, 0.075 mL of 20% hydrochloric acid, and 0.3 mL of water are added to the reaction mixture, after which a saturated aqueous solution of sodium hydrogencarbonate is added to render the solution alkaline, and the organic layer is extracted with ethyl acetate and dried with anhydrous magnesium sulfate. The solvent is distilled off, and the crude product thus obtained is refined by TLC (developing solvent was chloroform:methanol=19:1), which gives 21 mg of (6-hydroxy-2-cyclopentylbenzo[b]thien-3-yl)[4-[2-(dimethylamino) ethoxy]phenyl]methanone.

$^1$H-NMR(CD$_3$OD,$\delta$): 1.24–2,27 (8H,m), 2.37 (6H, s), 2,81 (2H, t,J=5.5 Hz), 4.18 (2H, t, J=5.5 Hz), 6.68–7.87(7H,m). MS(m/z): 409(M+), 58.

The following compounds may be synthesized in the same manner as in Example 7.

(6-hydroxy-2-cyclopentylbenzo[b]thien-3-yl)[4-[2-(diethylamino)ethoxy]phenyl]methanone
(6-hydroxy-2-cyclopentylbenzo[b]thien-3-yl)[4-[2-(1-pyrrolidinyl)ethoxy]phenyl]methanone
(6-hydroxy-2-cyclopentylbenzo[b]thien-3-yl)[4-[2-(1-homopiperidinyl)ethoxy]phenyl]methanone
(6-hydroxy-2-cyclopentylbenzo[b]thien-3-yl)[4-[2-[1-(3-methylpiperidinyl)]ethoxy]phenyl]methanone
(6-hydroxy-2-cyclohexylbenzo[b]thien-3-yl)[4-[2-(dimethylamino)ethoxy]phenyl]methanone
(6-hydroxy-2-cyclohexylbenzo[b]thien-3-yl)[4-[2-(diethylamino)ethoxy]phenyl]methanone
(6-hydroxy-2-cyclohexylbenzo[b]thien-3-yl)[4-[2-(1-pyrrolidinyl)ethoxy]phenyl]methanone
(6-hydroxy-2-cyclohexylbenzo[b]thien-3-yl)[4-[2-(1-piperidinyl)ethoxy]phenyl]methanone
(6-hydroxy-2-cyclohexylbenzo[b]thien-3-yl)[4-[2-(1-homopiperidinyl)ethoxy]phenyl]methanone
(6-hydroxy-2-cyclohexylbenzo[b]thien-3-yl)[4-[2-(1-(3-methylpiperidinyl)]ethoxy]phenyl]methanone
(6-hydroxy-2-cyclohexylbenzo[b]thien-3-yl)[4-[2-(N-morpholinyl) ethoxy]phenyl]methanone
(6-hydroxy-2-cyclohexylbenzo[b]thien-3-yl)[4-[2-[1-(4-methylpiperazinyl)]ethoxy]phenyl]methanone
(6-hydroxy-2-cyclohexylbenzo[b]thien-3-yl)[4-[2-[2-(1,2,3,4-tetrahydroisoquinolinyl)]ethoxy]phenyl]methanone
(6-hydroxy-2-cyclohexylbenzo[b]thien-3-yl)[4-[2-[1-(4-hydroxypeperidinyl) ethoxy]phenyl]methanone
(6-hydroxy-2-cycloheptylbenzo[b]thien-3-yl)[4-[2-(dimethylamino)ethoxy]phenyl]methanone
(6-hydroxy-2-cycloheptylbenzo[b]thien-3-yl)[4-[2-(1-dimethylamino)ethoxy]phenyl]methanone
(6-hydroxy-2-cycloheptylbenzo[b]thien-3-yl)[4-[2-(1-pyrrolidinyl)ethoxy]phenyl]methanone
(6-hydroxy-2-cycloheptylbenzo[b]thien-3-yl)[4-[2-(1-piperidinyl)ethoxy]phenyl]methanone
(6-hydroxy-2-cycloheptylbenzo[b]thien-3-yl)[4-[2-(1-homopiperidinyl)ethoxy]phenyl]methanone
(6-hydroxy-2-cyclohexylbenzo[b]thien-3-yl)[4-[2-[1-(3-methylpiperidinyl)]ethoxy]phenyl]methanone
[6-hydroxy-2-(2-methylcyclohexyl)benzo[b]thien-3-yl][4-[2-(1-pyrrolidinyl) ethoxy]phenyl]methanone
[6-hydroxy-2-(2-methylcyclohexyl)benzo[b ]thien-3-yl][4-[2-(1-piperidinyl) ethoxy]phenyl]methanone
[6-hydroxy-2-(2-methylcyclohexyl)benzo[b]thien-3-yl][4-[2-(1-homopiperidinyl) ethoxy]phenyl]methanone
[6-hydroxy-1-(3-methylcyclohexyl)benzo[b]thien-3-yl][4-[2-(dimethylamino) ethoxy]phenyl]methanone
[6-hydroxy-2-(3-methylcyclohexyl)benzo[b]thien-3-yl][4-[2-(diethylamino)ethoxy]phenyl]methanone
[6-hydroxy-2-(3-methylcyclohexyl)benzo[b]thien-3-yl][4-[2-(1-pyrrolidinyl)ethoxy]phenyl]methanone
[6-hydroxy-2-(3-methylcyclohexyl)benzo[b]thien-3-yl][4-[2-(1-piperidinyl)ethoxy]phenyl]methanone
[6-hydroxy-2-(3-methylcyclohexyl)benzo[b]thien-3-yl][4-[2-(1-homopiperidinyl)ethoxy]phenyl]methanone
[6-hydroxy-2-(3-methylcyclohexyl)benzo[b]thien-3-yl][4-[2-(3-methylpiperidinyl)ethoxy]phenyl]methanone
[6-hydroxy-2-(4-methylcyclohexyl)benzo[b]thien-3-yl][4-[2-(1-piperidinyl)ethoxy]phenyl]methanone
[6-hydroxy-2-(1-methylcyclooctenyl)benzo[b]thien-3-yl][4-[2-(1-piperidinyl) ethoxy]phenyl]methanone
(6-hydroxy-2-methylbenzo[b]thien-3yl)[4-[2-(1-pyrrolidinyl)ethoxy]phenyl]methanone
(6-hydroxy-2-cyclopentylbenzo[b]thien-3-yl)[4-[3-(1-piperidinyl)propoxy]phenyl]methanone
(6-hydroxy-2-cyclohexylbenzo[b]thien-3-yl)[4-[3-(diethylamino)propoxy]phenyl]methanone
(6-hydroxy-2-cyclohexylbenzo[b]thien-3-yl)[4-[3-(1-pyrrolidinyl)propoxy]phenyl]methanone
(6-hydroxy-2-cyclohexylbenzo[b]thien-3-yl)[4-[3-(1-piperidinyl)propoxy]phenyl]methanone
(6-hydroxy-2-cyclohexylbenzo[b]thien-3-yl)[4-[3-(1-homopiperidinyl)propoxy]phenyl]methanone
(6-hydroxy-2-cyclohexylbenzo[b]thien-3-yl)[4-[3-[1-(3-methylpiperidinyl)]propoxy]methanone
(6-hydroxy-2-cyclohexylbenzo[b]thien-3-yl)[4-[3-(N-morpholinyl)propoxy]phenyl]methanone
(6-hydroxy-2-cyclohexylbenzo[b]thien-3-yl)[4-[3-[1-(4methylpiperazinyl)]propoxy]phenyl]methanone
(6-hydroxy-2-cyclohexylbenzo[b]thien-3-yl)[4-[3-[2-(1,2,3,4-tetrahydroisoquinolinyl)]propoxy]phenyl]methanone
(6-hydroxy-2-cycloheptylbenzo[b]thien-3-yl)[4-[3-(1-pyrrolidinyl) propoxy]phenyl]methanone
(6-hydroxy-2-cycloheptylbenzo[b]thien-3-yl)[4-[3-(1-piperidinyl)propoxy]phenyl]methanone
(6-hydroxy-2-cycloheptylbenzo[b]thien-3-yl)[4-[3-(1-homopiperidinyl)propoxy]phenyl]methanone
(6-hydroxy-2-cyclohexylbenzo[b]thien-3-yl)[4-[2-(1-piperidinylcarbonyl)ethyl]phenyl]methanone
(6-hydroxy-2-cyclohexylbenzo[b]thien-3-yl)[4-[3-(1-piperidinyl)propyl]phenyl]methanone
(6-hydroxy-2-cycloheptylbenzo[b]thien-3-yl)[4-[2-(1-piperidinylcarbonyl)ethyl]phenyl]methanone (6-hydroxy-2-cycloheptylbenzo[b]thien-3-yl)[4-[3-(1-piperidinyl)propyl]phenyl]methanone
(6-hydroxy-2-cyclohexylbenzo[b]thien-3-yl)[4-[3-(dimethylamino)propyl]phenyl]methanone
(6-hydroxy-2-cyclopentylbenzo[b]thien-3-yl)[4-[2-(1-piperidinylcarbonyl)ethoxy]phenyl]methanone
[6-hydroxy-2-(4-hydroxycyclohexyl)benzo[b]thien-3-yl][4-[2-(1-piperidinyl)ethoxy]phenyl]methanone
(6-hydroxy-2-cyclododecylbenzo[b]thien-3-yl)[4-[2-(1-piperidinyl)ethoxy]phenyl]methanone
(6-hydroxy-2-isopropylbenzo[b]thien-3-yl)[4-[2-(1-piperidinyl)ethoxy]phenyl]methanone
(6-hydroxy-2-isopropylbenzo[b]thien-3-yl)[4-[2-(1-pyrrolidinyl)ethoxy]phenyl]methanone
(6-hydroxy-2-cyclohexylbenzo[b]thien-3-yl)[4-[2-(1-pyrrolidinylcarbonyl)ethyl]phenyl]methanone
(6-hydroxy-2-cyclohexylbenzo[b]thien-3-yl)[4-[3-(1-pyrrolidinyl)propyl]phenyl]methanone
[6-hydroxy-2-(2-methylcyclohexyl)benzo[b]thien-3yl][4-[2-)1-pyrrolidinylcarbonyl)ethyl]phenyl]methanone
(6-hydroxy-2-cycloheptylbenzo[b]thien-3-yl)[4-[2-(1-pyrrolidinylcarbonyl)ethyl]phenyl]methanone
(6-hydroxy-2-cyclohexylbenzo[b]thien-3-yl)[4-[3-(1-pyrrolidinyl)propyl]phenyl]methanone
(6-hydroxy-2-cyclohexylbenzo[b]thien-3-yl)[4-[4-(1-pyrrolidinyl)butyl]phenyl]methanone
(6-hydroxy-2-cyclohexylbenzo[b]thien-3-yl)[4-[3-(1-piperidinylcarbonyl)propyl]phenyl]methanone
(6-hydroxy-2-cyclohexylbenzo[b]thien-3-yl)[4-[4-(1-piperidinyl)butyl]phenyl]methanone

EXAMPLE 8

27 mg of (6-hydroxy-2-cyclohexylbenzo[b]thien-3yl)[4-[2-(1-piperidinyl)ethoxy]phenyl]methanone is dissolved in 1mL of pyridine, 0.1 mL of benzoyl chloride is added, and this mixture is agitated for one hour at room temperature. Ice is added to the reaction mixture, and the system is agitated for one hour. The organic layer is extracted with ethyl acetate and dried with anhydrous magnesium sulfate. The solvent is distilled off, and the crude product thus obtained is refined by TLC (developing solvent was chloroform:methanol=9: 1), which gives 37 mg of (6-benzoyloxy-2-cyclohexylbenzo[b]thien-3-yl)[4-[2-(1-piperidinyl)ethoxy]phenyl]methanone.

$^1$H-NMR(CD$_3$OD,δ): 1.17–1.96(16H,m), 2.62–2.73 (4H,m), 2.92 (2H, t, J=5.6 Hz), 4.25 (2H, t,J=5.6 Hz), 6.98–8.22 (12H, m). MS (m/z): 567 (M+), 98.

The following compounds may be synthesized in the same manner as in Example 8.
(6-dimethylcarbamoyloxy-2-cyclohexylbenzo[b]thien-3-yl) [4-[2-(1-piperidinyl)ethoxy]phenyl]methanone
(6-benzoyloxy-2-cyclohexylbenzo[b]thien-3-yl)[4-[2-(1-pyrrolidinyl)ethoxy]phenyl]methanone
(6-benzoyloxy-2-cycloheptylbenzo[b]thien-3-yl)[4-[3-(1-piperidinyl)propoxy]phenyl]methanone
(6-benzoyloxy-2-cycloheptylbenzo[b]thien-3-yl)[4-[3-(1-homopiperidinyl)propoxy]phenyl]methanone
(6-benzoyloxy-2-cycloheptylbenzo[b]thien-3-yl)[4-[3-(1-pyrrolidinyl)propoxy]phenyl]methanone

EXAMPLE 9

A mixture of 10 mg of (6-hydroxy-2-(4-hydroxycyclohexyl)benzo[b]thien-3-yl][4-[2-(1-piperidinyl)ethoxy]phenyl]methanone, 0.5 mL of acetic anhydride, and 0.5 mL of pyridine is agitated for 18 hours at room temperature. Ice is added to the reaction mixture, and the system is agitated for 30 minutes, after which the organic layer is extracted with ethyl acetate, washed with water and a saturated aqueous solution of sodium hydrogencarbonate, and dried with anhydrous magnesium sulfate. The solvent is distilled off, and the crude product thus obtained is refined by TLC (developing solvent was chloroform:methanol=9:1), which gives 5 mg of[6-acetoxy-2-(4-acetoxycyclohexyl)benzo[b]thien-3-yl][4-[2-(1-piperidinyl)ethoxy]phenyl]methanone.

$^1$H=NMR(CDCL$_3$,): 1.10–2.20(14H,m), 2.01(3H,s), 2.31(3H,2), 2.60–2.90(4H,m), 3.03(2H, t, J=6 Hz), 4.36(2H, t, J=6 Hz), 4.70 (1H, m), 6.80–7.60(5 h, m), 7.80 (2H, d, J+8.8 Hz). MS(m/z): 563(M+), 452, 434, 393, 351, 309, 98.

The following compound may be synthesized in the same manner as in Example 9.
(6-acetoxy-2-cyclohexylbenzo[b]thien-3-yl)[4-[2-(1-piperidinyl)ethoxy]phenyl]methanone.

We claim:

1. A method of inhibiting bone loss comprising administering to a human in need of treatment an effective amount of a compound having the formula

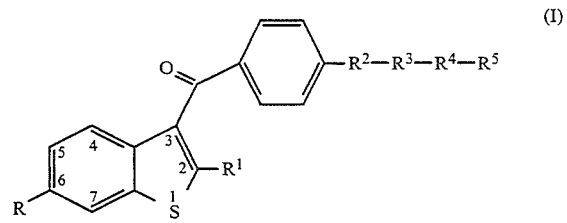

wherein R is hydrogen; hydroxy; $C_1$-$C_6$ alkoxy; a group of the formula —O—C(O)—R$^a$, wherein R$^a$ is hydrogen, $C_1$-$C_6$ alkyl optionally substituted with amino, halo, carbonyl, $C_1$-$C_6$ alkoxycarbonyl, $C_1$-$C_7$ alkanoyloxy, carbamoyl and/or aryl; or R$^a$ is $C_1$-$C_6$ alkenyl optionally substituted with aryl; or R$^a$ is a $C_3$-$C_7$ cycloalkyl; or R$^a$ is aryl optionally substituted with hydroxy, $C_1$-$C_6$ alkyl, $C_1$-$C_6$ alkoxy, and/or halo; or R$^a$ is —O—aryl, said aryl optionally substituted with hydroxy $C_1$-$C_6$ alkyl, $C_1$-$C_6$ alkoxy, and/or halo, or R is a group of the formula —O—SO$_2$—R$^b$ wherein R$^b$ may be $C_1$-$C_6$ alkyl or aryl optionally substituted with $C_1$-C6 alkyl;

or R is carbamoyloxy wherein the nitrogen may be substituted once or twice with $C_1$-C6 alkyl;

or R is a group of the formula —O—C(O)R$^c$—O—($C_1$-$C_6$ alkyl) wherein R$^c$ is a bond or $C_1$-$C_6$ alkanediyl;

R$^1$ is halo, $C_1$-$C_6$ alkyl, $C_1$-$C_7$ alkyl substituted with $C_1$-$C_6$ alkyl, substituted or unsubstituted $C_3$-$C_7$ cycloalkyl, or substituted or unsubstituted $C_3$-$C_7$ cycloalkenyl;

R$^2$ is O or CH$_2$;

R$^3$ is CH$_2$ or (CH$_2$)$_2$;

R$^4$ is

CH$_2$, or a bond; and

R$^5$ is amino, nitrilo optionally substituted once or twice with $C_1$-$C_6$ alkyl; or an N-heterocyclic ring which optionally has another hetero atom selected from N, O or S in said ring; or a pharmaceutically acceptable salt or solvate thereof.

2. A method of claim 1 wherein the human is a female.

3. A method of claim 2 wherein the female is estrogen deficient.

4. A method of claim 3 wherein the female is postmenopausal.

5. A method according to claim 1 wherein $R^1$ is a group having the formula

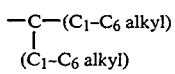

or a cycloalkyl group with a carbon number of three to eight that may be substituted with $C_1$–$C_6$ alkyl or hydroxy.

6. A method of claim 5 wherein R is hydroxy.

7. A method according to claim 6 wherein $R^2$ is O and $R^4$ is $CH_2$.

8. The method according to claim 1 wherein said compound is (6-hydroxy-2-cyclohexylbenzo[b]thien-3-yl)[4-[2-(1-pyrrolidinyl)ethoxy]phenyl]methanone, (6-hydroxy-2-cyclohexylbenzo[b]thien-3-yl)[4-[2-(1piperidinyl)ethoxy]phenyl]methanone, (6-hydroxy-2-cycloheptylbenzo[b]thien-3-yl)[4-[2-(1-pyrrolidinyl)ethoxy]phenyl]methanone, (6-hydroxy-2-cycloheptylbenzo[b]thien-3-yl)[4-[2-(1-piperidinyl)ethoxy]phenyl]methanone, (6-hydroxy-2-isopropylbenzo[b]thien-3-yl)[4-[2-(1-pyrrolidinyl)ethoxy]phenyl]methanone, or (6-hydroxy-2-isopropylbenzo[b]thien-3-yl)[4-[2-(1-piperidinyl)ethoxy]phenyl]methanone.

9. The method according to claim 6 wherein $R^2$ is $CH_2$.

10. The method according to claim 9 wherein said compound is (6-hydroxy-2-cyclohexylbenzo[b]thien-3-yl)[4-[3-(1-pyrrolidinyl)propyl]phenyl]methanone, (6-hydroxy-2cyclohexylbenzo[b]thien-3-yl)[4-[3-(1-piperidinyl)propyl]phenyl]methanone, or (6-hydroxy-2cyclohexylbenzo[b]thien-3-yl)[4-[2-(1-pyrrolidinylcarbonyl)ethyl]phenyl]methanone.

11. The method according to claim 5 wherein R is $C_1$–$C_6$alkoxy.

12. The method according to claim 11, wherein said compound is (6-methoxy-2-cyclohexylbenzo[b]thien-3-yl)[4-[2-(1-piperidinyl)ethoxy]phenyl]methanone or (6-acetoxy-2-cyclohexylbenzo[b]thien-3-yl)[4-[2-(1-piperidinyl)ethoxy]phenyl]methanone.

* * * * *

UNITED STATES PATENT AND TRADEMARK OFFICE
CERTIFICATE OF CORRECTION

PATENT NO.     :  5,441,964

DATED          :  August 15, 1995

INVENTOR(S)    :  Henry Uhlman Bryant et al.

It is certified that an error appears in the above-identified patent and that said Letters Patent is hereby corrected as shown below:

Column 2, line 14, delete ", nitrilo".

Column 18, line 66, delete ", nitrilo".

Signed and Sealed this

Twenty-ninth Day of July, 1997

Attest:

BRUCE LEHMAN

Attesting Officer          Commissioner of Patents and Trademarks